United States Patent
Ray

(10) Patent No.: US 6,835,049 B2
(45) Date of Patent: Dec. 28, 2004

(54) OCCLUSION DETECTOR FOR ROTARY PERISTALTIC PUMP

(75) Inventor: Claude Ray, Montezillon (CH)

(73) Assignee: Precimedix S.A., Neuchatel (CH)

( * ) Notice: Subject to any disclaimer, the term of this patent is extended or adjusted under 35 U.S.C. 154(b) by 0 days.

(21) Appl. No.: 10/250,706

(22) PCT Filed: Jan. 24, 2002

(86) PCT No.: PCT/CH02/00038

§ 371 (c)(1),
(2), (4) Date: Jul. 8, 2003

(87) PCT Pub. No.: WO02/061281

PCT Pub. Date: Aug. 8, 2002

(65) Prior Publication Data

US 2004/0057838 A1 Mar. 25, 2004

(30) Foreign Application Priority Data

Jan. 31, 2001 (EP) .............................................. 01810096

(51) Int. Cl.[7] .............................. F04B 49/00; A61M 1/00
(52) U.S. Cl. ......................... 417/63; 417/477.2; 73/168; 604/153
(58) Field of Search ............................... 417/63, 477.2, 417/977.1; 604/151, 153; 73/168

(56) References Cited

U.S. PATENT DOCUMENTS

| 5,215,450 | A | | 6/1993 | Tamari ........................ 417/474 |
| 5,657,000 | A | * | 8/1997 | Ellingboe .................... 340/608 |
| 5,791,881 | A | | 8/1998 | Moubayed et al. ........... 417/63 |
| 6,109,895 | A | | 8/2000 | Ray et al. ................. 417/477.2 |
| 6,149,394 | A | | 11/2000 | Allen ........................... 417/63 |
| 6,203,296 | B1 | * | 3/2001 | Ray et al. ................. 417/477.7 |
| 2003/0070486 | A1 | * | 4/2003 | Malmstrom et al. .......... 73/705 |

FOREIGN PATENT DOCUMENTS

| EP | 0 745 400 | 12/1996 | .......... A61M/5/142 |
| FR | 2 753 235 | 3/1998 | ........... F04B/43/12 |

* cited by examiner

Primary Examiner—Charles G. Freay
(74) Attorney, Agent, or Firm—Van Tassel & Associates

(57) ABSTRACT

The invention concerns a detector for detecting malfunction in a peristaltic pump wherein a flexible tubing (44) containing a fluid is locally compressed against a support part by rollers (32) mounted on a rotor (28) driven by a motor. Said detector is characterized in that it comprises: a ring (68) mounted sliding on the tubing between two extreme positions; driving means (64, 80, 84), actuated by the rotor, for subjecting said ring to a specific reciprocating motion between said positions; and detection means (74a, 74b, 84) reacting to an abnormal reciprocal motion by producing a warning signal.

15 Claims, 4 Drawing Sheets

OCCLUSION DETECTOR FOR ROTARY PERISTALTIC PUMP

Figure 1:
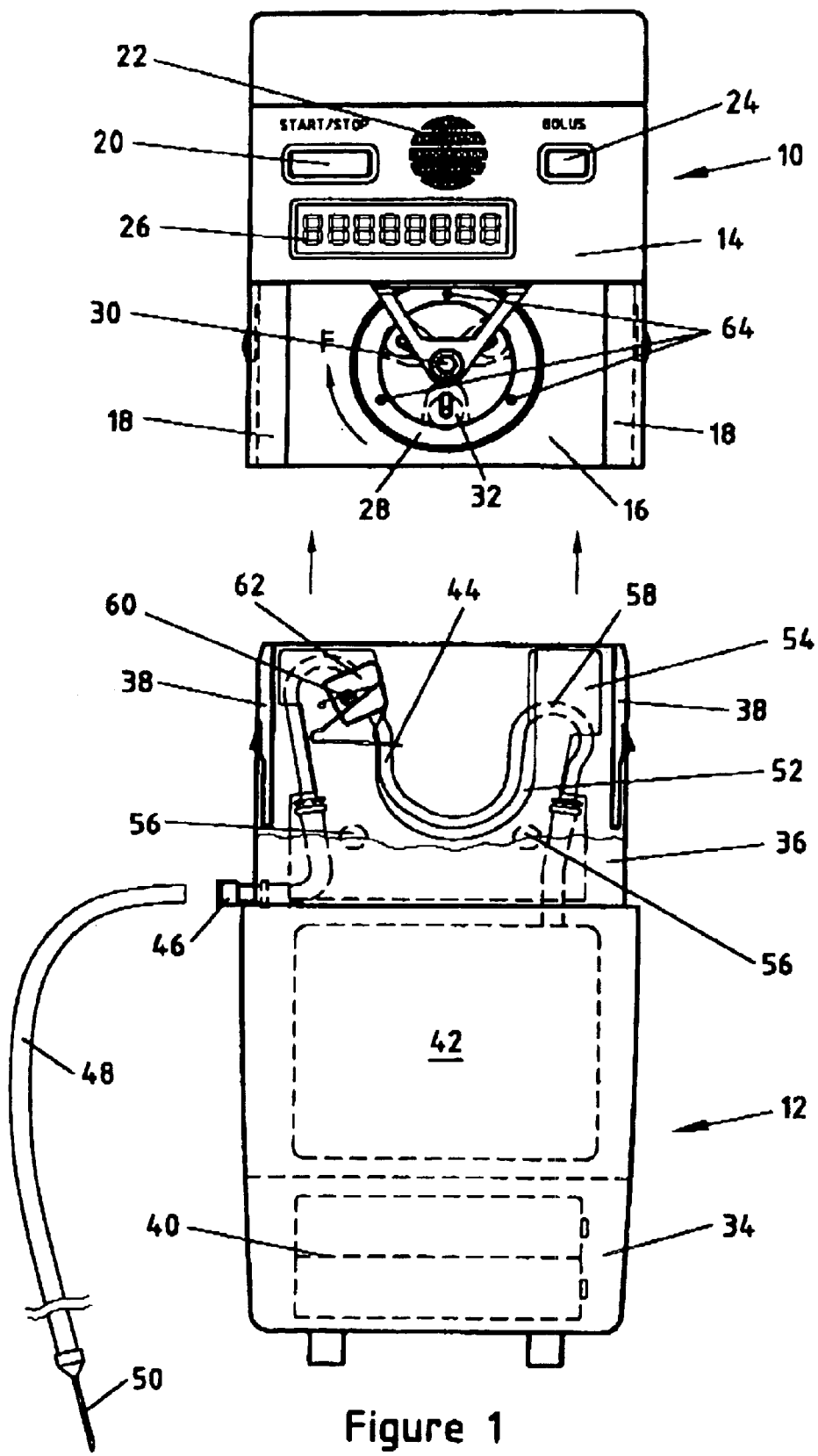

The present invention relates to rotary peristaltic pumps. It concerns, more particularly, a malfunction detector particularly malfunction due to an occlusion, in a miniaturized rotary peristaltic pump intended for injecting solutions of drugs.

Miniaturized pumps for medical use have been known for several years. Light and of small dimensions, they are carried by the patient discreetly and without to discomfort, allowing him to administer, subcutaneously or intravenously, continuously or in accordance with a determined program, controlled quantities of drug solutions, without however being confined to bed and connected to a bulky, expensive and noisy machine.

Such pumps are often of the rotary peristaltic type. Their principle consists in arranging a tubing of deformable plastic material connected to a reservoir containing the drug solution and locally compressing it against a support part of rounded shape by means of rollers mounted on a rotor driven by a motor acting via a gear train. The liquid is thus sucked from the reservoir and pushed towards the outlet to be injected into the patient's body.

FR Patent No. 2 753 235, for example, discloses a pump of this type.

When such pumps are designed, it is particularly important to concern oneself with the problem that can arise from occlusion of the tubing either because it is accidentally pinched or because the patient's body opposes injection of the medicine. It is just as important to ensure that the rotor itself is not stopped and that it rotates properly. In both cases, it is, thus, necessary to trigger an alarm informing the patient that the injection is not occurring normally so that he immediately alerts the persons responsible.

It is an object of the present invention to provide a detector for detecting malfunction in the pump, particularly caused by an occlusion of its tubing, which is both reliable and has a low cost price.

More precisely, the invention concerns a detector for detecting malfunction in a peristaltic pump wherein a flexible tubing containing a fluid is locally compressed against a support part by means of rollers mounted on a rotor driven by a motor, this detector being characterized in that it includes:
   a ring mounted so as to slide on the tubing between two extreme positions,
   drive means, actuated by the rotor, for subjecting said ring to a specific reciprocating motion between said positions, and
   detection means reacting to an abnormal reciprocating motion of the ring by producing an alarm signal Preferably, the internal diameter of the ring is such that it slides freely on the flexible tubing as long as the fluid that it is conveying flows normally, but such that its movement is stopped when, because of an occlusion, the fluid no longer flows normally and causes the tubing to swell. It is then advantageous for the tubing to have locally, in the portion thereof on which the ring travels, a thinned wall such that in the event of occlusion, the swelling will occur at that location.

According to a preferred embodiment, the drive means include:
   at least one stud attached to the rotor;
   a drive member activated by said stud on a part of its travel and acting in turn on the ring to move it, in one direction, from its first to its second extreme position, and
   a spring acting on the ring to move it, in the opposite direction, as soon as it is no longer subjected to the action of the drive member, from its second to its first extreme position.

The aforementioned drive member is, advantageously, a V-shaped spring, whose tip is fixed, one of whose branches Is activated by said stud and whose other branch acts on the ring.

Preferably, the drive means include three studs arranged at 120° from each other on the rotor.

Advantageously, the detection means include:
   a first switch closed by the ring when the latter is in its first position and open as soon as it is no longer in that position,
   a second switch closed by the ring when the latter is in its second position and open as soon as it is no longer in that position, and
   a circuit that has, in its memory, data representative of the moments at which said switches have to close and open when the reciprocating motion of the ring occurs according to a determined rhythm corresponding to proper operation of the pump, and whose function is to:
      produce data representative of the moments at which closing and opening of the switches occurs,
      compare the data contained in the memory with the data from the switches, and
      produce said alarm signal when the difference between the actual switch opening and closing moments and the opening and closing moments contained in the memory exceeds a determined value corresponding to abnormal operation of the pump.

According to a preferred embodiment, said moments are those at which the ring successively:
   leaves its first position,
   reaches its second position,
   leaves this second position, and
   returns to the first position.

Preferably, said motor is a stepping motor controlled by drive pulses and said data is the number of drive pulses provided to the motor, from the moment when the ring leaves its first position, so that the latter reaches its second position, leaves this position then returns to the first position.

The ring is, advantageously, made of metal and said switches include two fixed terminals against which the ring is applied when it occupies respectively its two extreme positions, and a mobil terminal attached to the ring.

Figure 2:
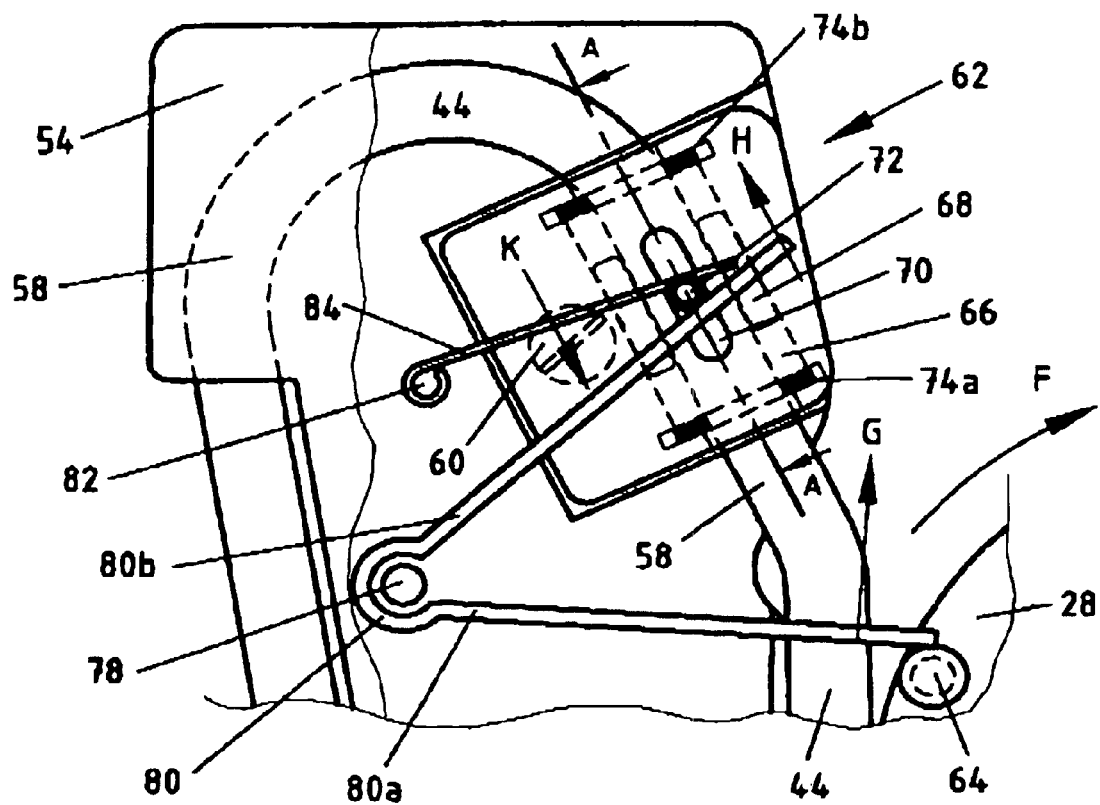
Figure 3:
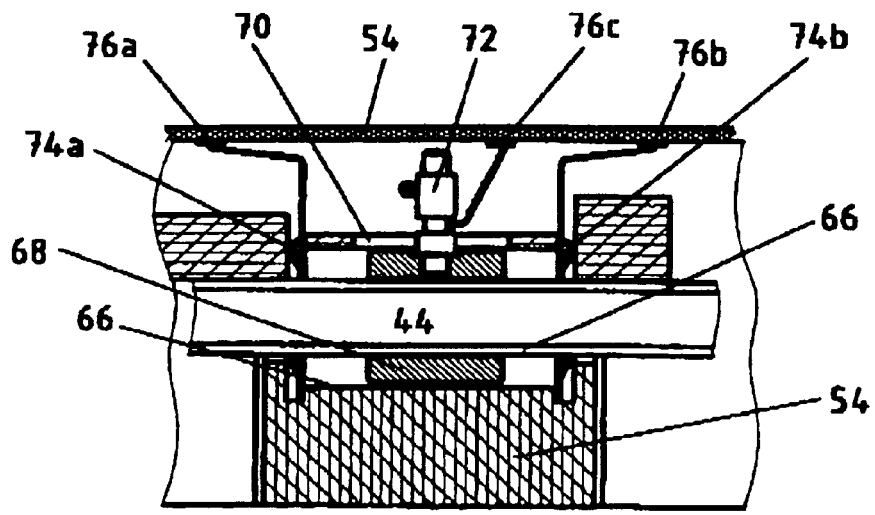
Figure 4A:
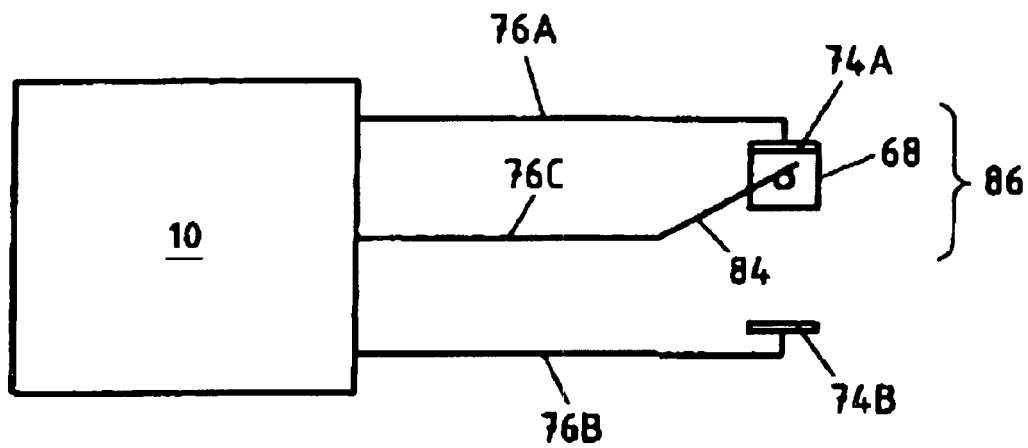
Figure 4B:
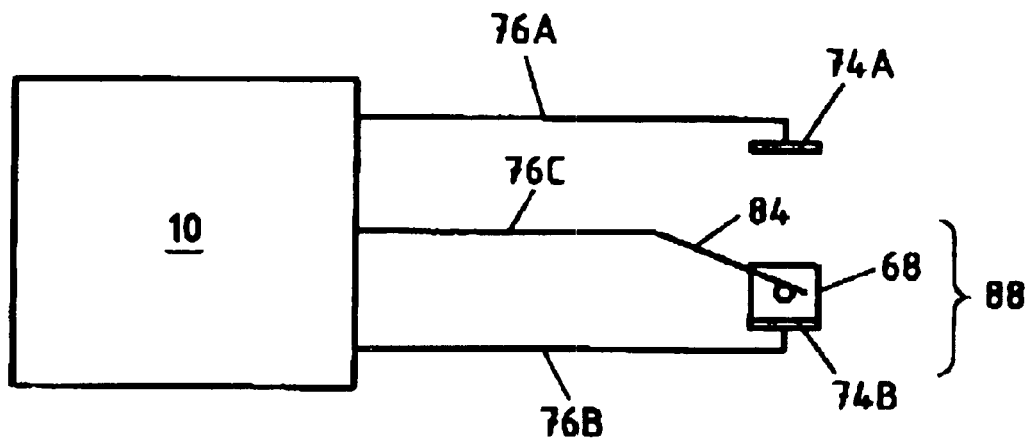
Figure 5:
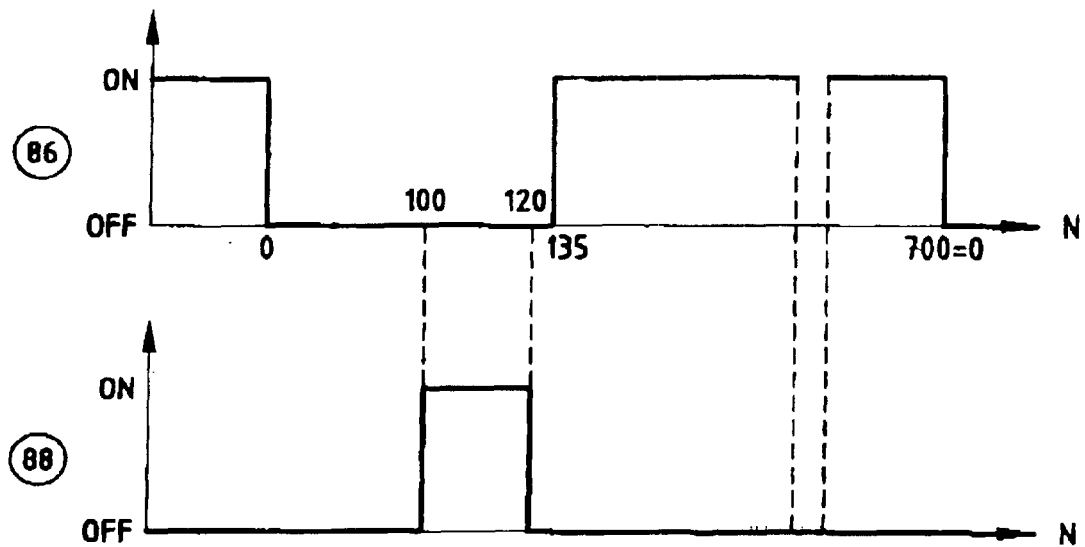
Figure 6:
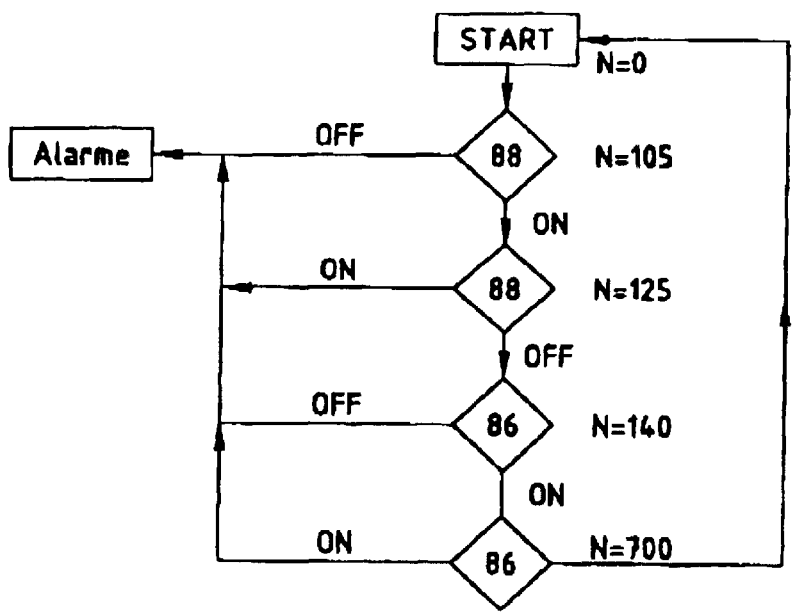

Other features of the invention will appear from the following description, made with reference to the annexed drawing, in which:

FIG. 1 is an overall view of a peristaltic pump fitted with a detector according to the invention, FIG. 2 is an enlarged view of the place on the pump where the mechanical detector part Is located, FIG. 3 is a cross-section of the detector along A—A, FIG. 4 is a schematic diagram showing the connection of the mechanical part of the detector to its electronic part, FIG. 5 is used to explain the operation of the detector, and finally, FIG. 6 shows the sequence of operations carried out in the electronic part of the detector.

Reference will be made, first of all, to FIG. 1, which shows a peristaltic pump with a cassette for injecting liquid drugs. This pump is formed of a pump module 10 and a cassette 12, which are assembled in a removable manner.

The pump itself is described, in great detail, particularly in the aforecited FR Patent No. 2 753 235. The present description will thus be limited to the essential elements of the pump.

In short, then, pump module 10 includes a rigid plastic casing 14 whose cassette side part has only a bottom 16 and two parallel lateral slide-ways 18 used for setting cassette 12 in place like a drawer.

On its top face, casing 14 includes a START/STOP button 20 used for controlling the starting and stopping of the pump, a warning acoustic alarm 22, a BOLUS button 24 used for starting administration of additional doses of the drug and an LCD display 26.

The casing allows a rotor 28 to appear between its two slide-ways, mounted so as to rotate freely about a shaft 30 fixed to the bottom of the casing and driven in rotation by means of a motor via a gear train (not visible in the Figure).

Rotor 28 carries three cylindrical rollers 32 arranged at 120° from each other and mounted so as to rotate freely about shafts parallel to shaft 30.

Cassette 12 includes a rigid plastic casing 34 whose part on the pump module side has only a top face 36 and two parallel lateral arms 38, intended to be inserted into slide-ways 18 of pump module 10. The rest of cassette 12 is occupied by two batteries 40 and a plastic pouch 42 filled with a liquid drug, all arranged under covers.

The electrical connection between cassette 12 and pump module 10 is assured by conductive paths (not shown) deposited on their respective cases.

Pouch 42 is connected to a plastic tubing 44 which occupies a place between the two arms 38 and whose end opens outside the cassette where it is occluded by a plug 46. This plug will be removed at the moment when the pump is to be used in order to allow a flexible tubing 48, ending in an injection needle 50, to be connected.

In the portion comprised between arms 38, tubing 44 is applied against a rounded U-shaped support part 52 whose radius is slightly greater than that of the circle traveled by the external face of rollers 32. Part 52 forms part of a rigid plastic plate 54 fixed underneath the top face 36 by snap fitting onto two studs 56. During rotation of rotor 28 in the direction of arrow F, its three rollers 32 compress tubing 44 against this U-shaped part 52, thereby pushing the liquid contained in pouch 42 towards the exterior, by a peristaltic movement.

Plate 54 is pierced, on each side of support part 52, by a channel 58, in which tubing 44 is arranged.

Fixed to plate 54 by a screw 60 and mounted on tubing 44 downstream from support part 52, there is an element 62, whose function is to detect any obstruction to the injection of the liquid drug Into the patient's body and to react to it by triggering acoustic alarm 22 and writing a message on LCD display 26.

It is important to note that the portion of tubing 44 that is subjected to the action of rollers 32 through element 62, has a reduced external diameter that gives it further flexibility, in order, not only to facilitate its compression by the rollers, but also to allow it to swell In the event of occlusion downstream.

It will also be noted that rotor 28 carries, on its top face, three metallic studs 64 arranged at 120° from each other and used, as will now be described in detail, for actuating detection element 62.

In FIGS. 2 and 3, it can be seen that element 62, made of rigid plastic, is arranged inside a housing made in the top face of plate 54. The bottom of this housing includes a semi-cylindrical groove which, with an identical groove formed at the base of element 62, delimits a cylindrical channel 66 opening out, at both its ends, into channel 58 used as a guide for tubing 44, Channel 66 accommodates a ring 68, advantageously made of brass, which closely encircles tubing 44 in Its most flexible portion. The inner diameter of this ring is adjusted such that in the absence of any occlusion of the tubing downstream, which would have the effect of causing it to swell, it can freely slide thereon, but that in the event of swelling due to an occlusion, it is prevent from moving. As regards the external diameter of ring 68, this is slightly less than the diameter of channel 66 such that it in no way hinders its movement.

Element 62 is pierced, in its top part, by a longitudinal groove 70 parallel to the axis of its channel 66 and opening onto it. Moreover, ring 68 is attached to a shaft 72, made of brass or steel, which is perpendicular to its axis and passes through groove 70. The latter thus limits the travel of ring 68.

The two ends of channel 66 are each provided with a U-shaped metal contact strip 74A and 74B allowing the tubing to pass and against which ring 68 is applied when it is in one or other of its end of travel positions. Each of these strips constitutes a fixed terminal which is respectively connected to a conductive path 76A and 76B arranged on the bottom face of plate 54.

The latter carries a pin 78 used as a holding and pivoting point for a V-shaped metal leaf spring 80 one of whose arms 80a, during the progression of rotor 28 along F, is pushed at its end along G successively by the three studs 64. The end of the other arm 80b of the spring abuts against shaft 72 of ring 68, which it thus pushes along H, parallel to its axis, via the effect of studs 64.

The bottom face of plate 54 carries a second pin 82 used as a point of attachment to a metal leaf spring 84 whose end abuts against shaft 72 so as to exert a thrust thereon along K, in the opposite direction to that exerted by V-shaped spring 80. Leaf spring 84 constitutes a mobile terminal that is connected to a third conductive path 76C arranged on the bottom face of the plate.

As FIG. 4 shows, the three paths 76A, 76B and 76C end at pump module 10 whose control circuit has the role of observing the sequence of moments at which:

in accordance with FIG. 4a, ring 68 is abutting against fixed terminal 74A (first position), which electrically connects it to mobil terminal 84 and thus connects paths 76A and 76C to each other;

in accordance with FIG. 4b, ring 68 is abutting against fixed terminal 74B (second position), which electrically connects it to mobile terminal 84 and thus connects paths 76B and 76C to each other.

In FIG. 4, these two situations have been schematized showing that they correspond to the closing or opening of two switches 86 and 88.

The operation of the detector according to the invention will now be described using FIGS. 5 and 6, taking as an example a system wherein one complete revolution of rotor 28 corresponds to 2100 pulses applied to its motor. This means that one of the three studs 64 comes into contact with V-shaped spring 80 every 700 drive pulses.

The pump circuit has data stored in its memory representative of moments at which the closing and opening of switches 86 and 88 should occur when the reciprocating motion of the ring is carried out in accordance with a determined rhythm corresponding to proper operation of the pump. This circuit is preferably a microprocessor, whose function is to:

produce data representative of the moments at which the closing and opening of the two switches occurs, compare the data contained in the memory with the data from the switches, and produce said alarm signal when the difference between the actual opening and closing moments of the switches and the opening and closing moments contained in the memory exceed a determined value corresponding to abnormal operation of the pump.

According to a preferred embodiment, the circuit is interested in the moments at which ring 68 successively:

leaves its first position and thus opens switch 86,
reaches its second position and thus closes switch 88,
leaves this second position and thus opens switch 88, then
returns to the first position and thus closes switch 86.

In the example described, the motor is a stepping motor and the data contained in the memory is the number N of drive pulses provided to the motor, from the moment when the ring leaves its first position, so that the latter:

reaches its second position, namely for N=100;
leaves this position, namely for N=120,
returns to the first position, namely for N=135,
leaves this position, namely for N=700.

The circuit is thus provided with a counter for counting the pulses supplied to the motor.

One starts from a state where none of studs 64 act on V-shaped spring 80. Via the action of leaf spring 84, ring 68 is thus abutting against strip 74A. Switch 86 is thus closed (ON) and switch 88 open (OFF). The counter is then at 0.

As FIG. 6 shows, the cycle starts at the moment when one of studs 64, via spring 80, sets the ring in motion along H. On leaving strip 74A, it thus causes switch 86 to open, switch 88 remaining open. The circuit then starts to count the drive pulses.

At the $100^{th}$ pulse, if everything is normal, the ring arrives against strip 74B and thus causes switch 88 to close. However, if an occlusion of tubing 44 is causing it to swell, the ring is prevented from progressing normally and switch 88 does not close. If the latter is still open (OFF) at the $105^{th}$ pulse (N=105), it is because the ring is blocked due to a serious occlusion of the tubing. The circuit then reacts by triggering activation of the acoustic alarm 22 and writing a warning message on display 26. The person carrying the pump must then, in accordance with the instructions he has been given, stop the pump by pressing button 20 and contact the competent personnel.

If no anomaly has been detected, the $120^{th}$ pulse corresponds to the moment at which the end of V-shaped spring 80 leaves stud 64, which quickly sets the ring in motion along K via the action of leaf spring 84. Normally, switch 88 opens. However, if swelling of the tubing causes the ring to be immobilized, thus preventing switch 88 from opening, and if the latter is still closed (ON) at the $125^{th}$ pulse (N=125), the circuit triggers the alarm.

If nothing abnormal has happened, it is at the $135^{th}$ pulse that the ring has to return to strip 74A and cause switch 86 to close. But if, at the $140^{th}$ pulse (N=140), this switch is still open (OFF), this means that there is an occlusion of the tubing and causes the alarm to be triggered.

In the case of normal operation, via the action of leaf spring 84, the ring will then remain applied on strip 74A, switch 86 thus remaining closed (ON), until the next stud 64 sets the ring in motion again along H and thus causes switch 86 to reopen. This occurs normally with the $700^{th}$ pulse (N=700). But if, because of an occlusion, switch 86 remains closed (ON), the alarm is triggered. Conversely, if all is well, a new cycle then starts, identical to that which has just been described, after the counter has been rest to 0.

A detector that is both simple, reliable and inexpensive is thus achieved, which, while ensuring that the ring carries out its normal reciprocating motion, allows any occlusion of the tubing to be indicated. Of course, even if there is no occlusion opposing the movement of the ring, any malfunction of the pump (that can be imputed to the battery, motor, gear train or rotor) involving abnormal movement of the ring will also be detected and indicated.

The invention thus allows detection, not only of an occlusion of the tubing, but also a malfunction of the pump itself.

What is claimed is:

1. Detector for detecting malfunction in a peristaltic pump wherein a flexible tubing (44) containing a fluid is locally compressed against a support part (52) by means of rollers (32) mounted on a rotor (28) driven by a motor, characterized in that it includes:

a ring (68) mounted so as to slide on the tubing between two extreme positions, drive means (64, 80, 84), activated by the rotor, for subjecting said ring to a specific reciprocating motion between said positions, and detection means (86, 88) reacting to an abnormal reciprocating motion of the ring by producing an alarm signal.

2. Detector according to claim 1, characterized in that the internal diameter of the ring (68) is such that it slides freely on the flexible tubing (44) as long as the fluid flows normally, but that its movement is stopped when, because of an occlusion, the fluid no longer flows normally and causes the tubing (44) to swell.

3. Detector according to claim 2, characterized in that, in the portion in which the ring (68) travels, the tubing (44) has, locally, a thinned wall so that, in the event of occlusion, the swelling occurs at that location.

4. Detector according to claim 1, characterized in that said drive means include:

at least one stud (64) attached to the rotor (28);

a drive member (80) activated by said stud on a part of its travel and acting in turn on the ring to move it, in one direction, from its first to its second extreme position, and a spring (84) acting on the ring to move it, in the opposite direction, as soon as it is no longer subjected to the action of the drive member, from its second to its first extreme position.

5. Detector according to claim 4, characterized in that said drive member (80) is a V-shaped spring, whose tip is fixed, and one of whose branches (80a) is activated by said stud (64) and the other branch (80b) acts on the ring (68).

6. Detector according to claim 4, characterized in that the drive means include three studs (64) arranged at 120° from each other on the rotor.

7. Detector according to claim 1, characterized in that said detection means include:

a first switch (86) closed by the ring (68) when the latter is in its first position and open as soon as it is no longer in that position, a second switch (88) closed by the ring (68) when the latter is in its second position and open as soon as it is no longer in that position, and a circuit that has, in its memory, data representative of the moments at which said switches have to close and open when the reciprocating motion of the ring occurs according to a determined rhythm corresponding to proper operation of the pump, and whose function is to:
produce data representative of the moments at which closing and opening of the switches occurs,
compare the data contained in the memory with the data from the switches, and produce said alarm signal when the difference between the actual switch opening and closing moments and the opening and closing moments contained in the memory exceed a determined value corresponding to abnormal operation of the pump.

8. Detector according to claim 7, characterized in that said moments are those at which the ring successively:

leaves its first position, reaches its second position, leaves this second position, and returns to the first position.

9. Detector according to claim 7, characterized in that said motor is a stepping motor controlled by drive pulses and said data is the number of drive pulses provided to the motor, from the moment when the ring leaves its first position, so that the latter reaches its second position, leaves that position, then returns to the first position.

10. Detector according to claim 7, characterized in that the ring (68) is made of metal and in that said switches (86, 88) include two fixed terminals (74A, 74B) against which the ring is applied when it occupies respectively its two extreme positions, and a mobile terminal (84) attached to the ring.

11. Detector according to claim 5, characterized in that the drive means include three studs (64) arranged at 120° from each other on the rotor.

12. Detector according to claim 8, characterized in that said motor is a stepping motor controlled by drive pulses and said data is the number of drive pulses provided to the motor, from the moment when the ring leaves its first position, so that the latter reaches its second position, leaves that position, then returns to the first position.

13. Detector according to claim 8, characterized in that the ring (68) is made of metal and in that said switches (86, 88) include two fixed terminals (74A, 74B) against which the ring is applied when it occupies respectively its two extreme positions, and a mobile terminal (84) attached to the ring.

14. Detector according to claim 9, characterized in that the ring (68) is made of metal and in that said switches (86, 88) include two fixed terminals (74A, 74B) against which the ring is applied when it occupies respectively its two extreme positions, and a mobile terminal (84) attached to the ring.

15. Detector according to claim 12, characterized in that the ring (68) is made of metal and in that said switches (86, 88) include two fixed terminals (74A, 74B) against which the ring is applied when it occupies respectively its two extreme positions, and a mobile terminal (84) attached to the ring.

* * * * *